US008208651B2

(12) United States Patent
Boehme et al.

(10) Patent No.: US 8,208,651 B2

(45) Date of Patent: Jun. 26, 2012

(54) ACTIVE SOUND BLOCKER

(75) Inventors: Sten Boehme, Kiel (DE); Delf Sachau, Hamburg (DE); Thomas Kletschkowski, Hamburg (DE); Harald Breitbach, Hamburg (DE); Kai Simanowski, Hamburg (DE)

(73) Assignee: Airbus Operations GmbH, Hamburg (DE)

( * ) Notice: Subject to any disclaimer, the term of this patent is extended or adjusted under 35 U.S.C. 154(b) by 755 days.

(21) Appl. No.: 12/317,091

(22) Filed: Dec. 19, 2008

(65) Prior Publication Data

US 2009/0180627 A1 Jul. 16, 2009

Related U.S. Application Data

(60) Provisional application No. 61/008,741, filed on Dec. 21, 2007.

(30) Foreign Application Priority Data

Feb. 27, 2008 (DE) ......................... 10 2008 011 285

(51) Int. Cl.
*A61F 2/20* (2006.01)

(52) U.S. Cl. ................... 381/71.8; 381/71.14; 381/71.4; 381/71.7

(58) Field of Classification Search ................. 381/71.4, 381/71.7, 71.8, 71.14
See application file for complete search history.

(56) References Cited

U.S. PATENT DOCUMENTS 4,686,693 A * 8/1987 Ritter ........................... 381/73.1
5,416,844 A * 5/1995 Nakaji et al. ................. 381/71.4
5,488,667 A * 1/1996 Tamamura et al. .......... 381/71.4
5,493,616 A * 2/1996 Iidaka et al. ................. 381/71.4
5,551,650 A 9/1996 Southward et al.
6,041,126 A * 3/2000 Terai et al. .................... 381/71.6
6,654,467 B1 * 11/2003 York et al. ................. 381/71.14
6,690,800 B2 * 2/2004 Resnick ......................... 381/73.1
6,952,474 B2 * 10/2005 Wittke et al. ............. 379/406.02
6,978,010 B1 * 12/2005 Short et al. ............... 379/388.03
7,031,460 B1 * 4/2006 Zheng et al. ............. 379/406.06
7,058,185 B1 * 6/2006 Egelmeers et al. ............. 381/93
7,088,828 B1 * 8/2006 Bradford et al. ............. 381/71.1
7,809,129 B2 * 10/2010 Wu et al. .................. 379/406.01

(Continued)

FOREIGN PATENT DOCUMENTS

DE 19735649 3/1999
DE 102007012611 1/2009
EP 0884498 12/1998
EP 0916817 5/1999

OTHER PUBLICATIONS

C. H. Hansen: ,,Understanding active noise cancellation, Spon Press, London, 2001 S. 114-117.

(Continued)

*Primary Examiner* — David S. Warren

(74) *Attorney, Agent, or Firm* — Lerner, David, Littenberg, Krumholz & Mentlik, LLP

(57) ABSTRACT

A noise reduction system for actively blocking a noise source for a means of transport. The noise reduction system comprises at least one counter sound source and at least one intensity sensor. The at least one counter sound source and the at least one intensity sensor are arranged in a measuring region. In the measuring region, measuring of the noise intensity of the noise source and measuring of the counter sound intensity of the counter sound source are by the intensity sensor. Based on the measured noise intensity and the counter sound intensity, the counter sound source is controllable such that the sound energy input of the noise source can be globally reduced by the counter sound source.

10 Claims, 4 Drawing Sheets

U.S. PATENT DOCUMENTS

| | | | | |
|---|---|---|---|---|
| 7,835,774 | B1 * | 11/2010 | Appell et al. | 455/570 |
| 7,996,048 | B1 * | 8/2011 | Mikan et al. | 455/570 |
| 2006/0002570 | A1 * | 1/2006 | Vaudrey et al. | 381/92 |
| 2006/0029212 | A1 * | 2/2006 | Short et al. | 379/388.03 |
| 2006/0204015 | A1 * | 9/2006 | Ip et al. | 381/71.1 |
| 2007/0083361 | A1 * | 4/2007 | Ferencz et al. | 704/201 |
| 2008/0118081 | A1 * | 5/2008 | Chang | 381/94.1 |
| 2009/0034755 | A1 * | 2/2009 | Short et al. | 381/94.1 |
| 2010/0296666 | A1 * | 11/2010 | Lin | 381/71.6 |
| 2011/0093262 | A1 * | 4/2011 | Wittke et al. | 704/226 |
| 2011/0105034 | A1 * | 5/2011 | Senders et al. | 455/63.1 |
| 2011/0153320 | A1 * | 6/2011 | Kim et al. | 704/226 |

OTHER PUBLICATIONS

S. J. Elliott: „Signal processing for active control, Academic Press, San Diego, CA,S., 2001 S. 38-41,226-229,411-414.

J. Hald, A power controlled active noise cancellation technique (International Symposium on Active Noise Control of Sound and Vibration, S.285-290, 1991.

S. J. Elliott et al., Power output minimization and power absorption in the active control of sound (Journal of Acoustical Society of America 90(5), S.2501-2512, 1991.

S. D. Snyder: Active Noise Control Primer, American Institute of Physics, 2000.

* cited by examiner

ACTIVE SOUND BLOCKER

CROSS-REFERENCE TO RELATED APPLICATIONS

This application claims the benefit of the filing date of U.S. Provisional Patent Application No. 61/008,741 filed Dec. 21, 2007, the disclosure of which is hereby incorporated herein by reference.

BACKGROUND OF THE INVENTION

The present invention relates to a noise reduction system for actively blocking a noise source, and to a noise reduction method for actively blocking a noise source, for a means of transport, as well as to the use of a noise reduction system in a means of transport, and to a means of transport comprising a noise reduction system.

In many technical applications, as a result of machine noise, propeller noise or other interference, wave fields are induced in interior spaces, in particular in the low-frequency range (f<500 Hz).

Due to regulations relating to noise protection, or in order to increase the level of comfort, measures for noise abatement are frequently taken. At present a multitude of passive and active measures are available. In particular when applied in the field of low frequencies, active systems make it possible to achieve significant savings in weight and space; however, the effective use of active counter sound systems in interior spaces involves significant expenditure in the positioning of the actuators and sensors (S. J. Elliott: "Signal processing for active control", Academic Press, San Diego, Calif., 2001).

In many applications the harmonic interference sound, which is mostly stationary, is conveyed to an interior space by way of a limited number of transmission paths. These transmission paths comprise, for example, openings or vibrating structures. As a result of these, sound energy is transported into the interior space, which sound energy is, for example, measurable in the form of various sound values, for example the acoustic power of the acoustic pressure or the acoustic intensity.

Presently, a host of different methods for reducing the acoustic power radiated through a wall are known. Most of the methods are designed such that potential acoustic energy in an interior space can be reduced.

A reduction of the potential acoustic energies essentially requires a global distribution of microphones and loudspeakers. These microphones and loudspeakers are connected to a regulator that controls the loudspeakers such that the sound pressure and thus the potential acoustic energy at the microphones can be minimised. This requires a multitude of different components, for example microphones and loudspeakers, which have to be distributed in a targeted and expensive manner in order to achieve a significant noise reduction not only at a point but also in an entire interior space (S. D. Snyder: "Active noise control primer", American Institute of Physics, 2000).

For noise reduction in interior spaces it is also possible to damp the vibrating and noise-generating structures, for example the aircraft fuselage (S. D. Snyder: "Active noise control primer", American Institute of Physics, 2000). The forces which in this process have to be introduced into the vibrating structure can, in turn, reduce the lifespan life of the structure. Furthermore, there are difficulties relating to the control of the actuators necessary for this, because, for example, in aircraft engineering the use of piezoceramic actuators is not possible due to the capacity required and due to the approval conditions that have to be met. Furthermore, it is not inevitable that solely from a vibration amplitude of a vibrating structure deductions about its radiated acoustic performance can be drawn (F. Fahy, P. Gardonio: "Sound and structural vibration", Academic Press, Oxford, 2007).

Furthermore, the vibrations of the radiating structure can be reduced in that as the field variable to be minimised, the sound pressure at microphones distributed in the interior space is minimised. However, in this context the quality of the actuator technique used and of the distribution of the sensors plays a significant role, wherein implementation is made more difficult (C. H. Hansen: "Understanding active noise cancellation", Spon Press, London, 2001).

J. Hald in "A power controlled active noise cancellation technique" (International Symposium on Active Noise Control of Sound and Vibration, pp 285-290, 1991) shows a counter sound source in order to absorb the radiated energy of a noise source. However, the success of this method depends on the type of primary source, because additional absorption can cause the primary source to radiate more strongly so that the acoustic pressure level in the interior space is increased.

S. J. Elliott et al. in "Power output minimization and power absorption in the active control of sound" (Journal of Acoustical Society of America 90 (5), pp 2501-2512, 1991) describes a method for minimising the entire radiated output of sound sources and counter sound sources. As a prerequisite for this, the surface velocity of the sound must be known both of the noise source and of the counter sound source, which can result in considerable complexity of the measuring method.

BRIEF SUMMARY OF THE INVENTION

All known methods thus require a large number of microphones and loudspeakers whose placement must in part involve the use of complex methods. Furthermore, the described methods may fail if several primary sources make a non-negligible contribution to the induced sound field.

There may be a need to actively reduce disturbing noise in a means of transport.

According to an exemplary embodiment of the invention, a noise reduction system for actively blocking a noise source for a means of transport is provided as well as a method for actively blocking a noise source for a means of transport, and the use of a noise reduction system in a means of transport, as well as a means of transport comprising a noise reduction system with the characteristics according to the independent claims.

According to an exemplary embodiment of the invention, a noise reduction system for actively blocking a noise source for a means of transport is provided. In this arrangement the noise reduction system comprises at least one counter sound source and at least one intensity sensor. In this arrangement the at least one counter sound source and the at least one intensity sensor are arranged in a measuring region. In the measuring region, measuring of the noise intensity of the noise source and measuring of the counter sound intensity of the counter sound source can be provideable by the intensity sensor. Based on the measured noise intensity and on the counter sound intensity, the counter sound source is controllable such that the sound energy input of the noise source can be globally reduced by the counter sound source.

According to a further exemplary embodiment, a noise reduction method for actively blocking a noise source for a means of transport is provided. Firstly, at least one counter sound source and at least one intensity sensor are arranged in a measuring region. By the intensity sensor the noise intensity of the noise source and the counter sound intensity of the counter sound source in the measuring region are measured. Based on the measured noise intensity and on the counter sound intensity, the counter sound source is controlled such that the sound energy input of the noise source is globally reduced by the counter sound source.

According to a further exemplary embodiment, the noise reduction system is used in a means of transport.

According to a further exemplary embodiment, a means of transport with the noise reduction system described above is provided.

The term "counter sound source" can, for example, refer to loudspeaker equipment that can generate and emit a directed sound wave. In this arrangement the counter sound source can, for example, generate a particular acoustic power P that is defined by its acoustic intensity or its acoustic velocity and its sound pressure respectively. The sound intensity is the acoustic power that flows through a surface that is arranged perpendicular to the direction of propagation.

The term "intensity sensor" refers to measuring equipment that can measure sound intensity. The term "sound intensity I" refers to the sound energy overlay of a surface. The sound intensity I describes the energy inflow into sound fields in a point-shaped manner. The intensity I indicates the size of the energy contribution in a spatial point, and the direction in which the energy propagates there. The intensity I is calculated from the product of the acoustic velocity v and the acoustic pressure p:

$$\vec{I}=p\cdot\vec{v}$$

The term "measuring region" refers to the region in which the intensity sensor can still measure the intensity of a noise source and at the same time of a counter sound source. In other words, the measuring region defines the region in which the intensity sensor and the counter sound source should be arranged in order to measure a meaningful intensity value of the noise source and of the counter sound source. The measuring region can, for example, define one meter between the counter sound source and the noise source, but also a distance that is longer or shorter, as desired, for example ½ m, 30 cm, 20 cm or even 5 cm. Likewise, the measuring region can be defined so as to be infinitesimally small so that the counter sound source rests, for example, on the noise source or is in contact with it.

The term "sound energy input" of the noise source refers to the amount of energy of the sound that starting from the noise source in an interior space is radiated or introduced. In other words, lowering the sound energy input of the noise source in an interior space results in calming of the latter and in an increase of comfort.

In contrast to prior art, the present noise reduction system provides a device by which it is precisely not the potential acoustic energy in the interior space that is reduced, but instead the sound energy input in front of the noise source. As a consequence of this it is not the sound pressure as an adjustment variable of active sound blocking that is changed, but instead, by adjustable sound intensity, a sound energy input is blocked. According to the invention this is implemented in that at least one counter sound source, for example a loudspeaker, is coupled to a sound intensity sensor, for example to a pair of microphones, in order to in this way measure the sound intensity at the respective noise source, for example an area radiator or a sheet metal field. In this arrangement the loudspeaker is set up or positioned in a measuring region immediately in front of the noise source. The intensity sensor is placed in the measuring region such that said intensity sensor can measure the radiating intensity both from the noise source, in other words the noise intensity, and from the counter sound source, in other words the counter sound intensity. Based on these intensities, in other words the noise intensity and the counter noise intensity, the at least one counter sound source can be controlled such that the radiated acoustic performance, respectively the sound energy input of the noise source, and of the counter sound source is minimised. This leads to a reduction in the sound energy input in the interior space and thus to a global reduction of the acoustic pressure.

Below, the object of the invention is clarified by equations:

Generally speaking, the following applies to the radiated acoustic power of a noise source or of a counter sound source:

$$P=\int I_n dS.$$

The radiated acoustic power is designated by the character P. The radiating surface, for example the noise source, is designated by the character S. $I_n$ describes the mean acoustic intensity that represents the sum of all intensities measured at the intensity sensor, for example of the noise source and of the counter sound source. The intensity is a vectorial measured variable, i.e. in addition to the amount, the direction of the sound energy flow is indicated by a positive or negative operational sign. The intensity is calculated from the product of the direction-indicating sound velocity $\vec{v}$ and the sound pressure p:

$$\vec{I}=p\cdot\vec{v}.$$

If the entire radiated performance of two sound sources is considered, the following results:

$$P_{ges}=P_1+P_2$$

With the assumption that each point on the areas of the sound source radiates at the same intensity, the total radiated performance can be approximated with the following equation:

$$P_{ges}=S_1\cdot I_{m1}+S_2\cdot I_{m2}.$$

With the further assumption that the radiating areas of the sources are identical in size, the equation can be simplified as follows:

$$\frac{P_{ges}}{S}=I_{m1}+I_{m2}.$$

To effectively damp noise the counter sound source must influence the noise source such that the entire radiated power $P_{ges}$ is minimised. According to the above equation, a sound power $P_{ges}$ is switched off precisely when the sound level $P_{ges}$ per unit of area equals the sum of all intensities $I_{m1}+I_{m2}$. In other words, by the counter sound source an intensity needs to be generated which together with the measured noise intensity if at all possible achieves the value $P_{ges}$ per unit of area.

Minimisation of the sound intensity measured at the intensity sensor leads to minimisation of the radiated acoustic power P of the counter sound source and of the noise source located nearby or in the measuring region, for example a radiating part of an outer skin of an aircraft. This then results in global noise reduction.

In this arrangement the problem of positioning the actuators and the sound sensors is solved. Furthermore, the primary sources or the noise sources are prevented in a targeted manner from radiating sound, without this having an influence on other sources. In addition, the backlash to the radiating structure is negligible.

With the present invention disturbing noise can be actively blocked directly at the noise source without a disturbing noise energy input penetrating the interior space, for example of a passenger cabin. In known noise blocking methods an attempt is made to reduce the potential acoustic energy in an interior space by controlling the sound pressure. However, since the sound is independent of location, energy reduction by sound pressure can only be successfully carried out at the location at which a sound reduction is desired. For example, counter sound sources and sound pressure sensors need to be affixed directly at the position at which the sound or noise is to be reduced. In other words, this means that, for example in a passenger cabin, an active sound blocking device that comprises at least one counter sound source and a sound pressure measuring device must be used at the location of each passenger.

Consequently, for effective reduction of the sound in the entire interior space over the entire interior space a multitude, for example 200 to 400, of counter sound sources and of sound pressure sensors need to be arranged in order to achieve an effective reduction and damping of the sound.

By the present invention the sound energy input can be blocked directly at the source, for example at the exterior skin of an aircraft, in that the intensity which emanates in a directional manner from a particular noise source is actively blocked so that the disturbing noise does not enter the interior space in the first place. Thus, despite a sound blocking device that is arranged in a point-shaped manner, it is possible, by the intensity control method, to achieve global regulating success. With the present invention there is no need to provide a multitude of counter sound sources and sound pressure sensors that are necessary according to the sound-pressure methods. Thus, due to the small system size costs can be saved and, in particular, installation weight and installation space can be reduced.

According to a further exemplary embodiment, the intensity sensor is equipped such that the noise intensity and the counter sound intensity are measurable with a positive operational sign. As described above, the sound intensity comprises the product of sound velocity v and sound pressure P. The sound velocity v is direction-oriented. The sound velocity v is given a positive operational sign if the sound waves are propagated away from the noise source. If the sound velocity v has a negative operational sign, this means that the sound source absorbs sound so that graphically the directional arrows point towards the sound source. According to the present exemplary embodiment, the sound intensity sensor is equipped such that it measures the noise intensity and the sound intensity with a positive operational sign. It is thus possible to implement simpler regulation or control of the counter sound source. When measuring with a negative operational sign it is possible, for example as a result of the sound-absorbent effect of the counter sound source, to render control of the counter sound source more difficult, and even to achieve a noise-increasing effect.

According to a further exemplary embodiment, the intensity sensor is installed laterally or behind the at least one counter sound source. In this way, due to the proximity to the counter sound source an optimal measuring result of the intensity sensor can be made possible. If the intensity sensor is, for example, installed laterally or behind the counter sound source or its sound membrane, the at least one intensity sensor can measure the sum of both intensities, namely that of the noise source and of the counter sound source, and subsequently, from the sum of the intensities, can control the counter sound source such that the sound energy input of the noise source can better be reduced. According to a further exemplary embodiment, the at least one intensity sensor is designed to form an integral unit with the at least one counter sound source. It is thus possible to form integral or single-piece units that can be affixed in close proximity to the noise source without significant adjustment expenditure. Likewise, there is no longer a need for complex cabling and adjustment of the individual components. Consequently it is possible to save installation space and to reduce the time required for installation. Moreover, weight and costs can be saved.

According to a further exemplary embodiment, the counter sound source is equipped such that a direction of sound propagation of the counter sound source can be provided essentially in the direction of the noise source. If the counter sound source, which comprises, for example, a loudspeaker, is directed in the direction of the noise source, then in this way the control by way of the counter sound intensity can be improved without the counter sound source itself emitting noisy sounds into an interior space. It is thus possible to provide the radiated sound performance of the counter sound source so that it is directed towards the noise source so that the sound energy input of the noise source can be reduced more effectively.

According to a further exemplary embodiment, the counter sound source is equipped such that it covers the region of the greatest energy input of the noise source. It is thus possible, for example, to detect and measure a noise source in advance, and based on its greatest energy input the counter sound source can be placed. In this way effective noise reduction can be implemented. Furthermore, this provides the option of reducing the energy input of the noise source such that it becomes possible thereafter to detect further noise sources, because due to a multitude of noise sources often a mixed energy input arises that has an interfering effect in the positioning of other insulating materials or insulating systems.

According to a further exemplary embodiment, the intensity sensor is selected from the group comprising two-microphone techniques sensors and sound pressure/sound velocity sensors. In the two-microphone technique, two field sizes are measured, namely the sound pressure p (t) and the velocity component $v_m$ (t). Measuring the sound pressure can take place in a simple manner with the use of a measuring microphone. When determining the sound velocity it is possible, for example, to use miniature ultrasound transmitters and receivers. These are arranged in close proximity to each other in the direction of measuring. The frequency change in the ultrasound signal as a result of the Doppler effect, which frequency change occurs in the receiver signal, can then be used as a degree of the sound velocity. Furthermore, at two directly adjacent locations the sound pressure can be measured, and the differential coefficient can be formed. The sensors used in this arrangement comprise two microphones specially selected for their phase ratio, which microphones are arranged one beside the other at a short predetermined distance $\Delta r$, which microphones measure the two acoustic pressures $p_A$ and $p_B$ received at the two locations. Furthermore, acoustic velocity sensors are imaginable, for example so-called microflow sensors.

According to a further exemplary embodiment, the noise source is selected from the group comprising area radiators, sheet metal fields, aircraft fuselages, motor vehicle bodies and drive noises. By the noise reduction system described it is thus possible to actively reduce almost all point-shaped noise sources as well as area radiators. For example, a vibrating aircraft fuselage or its sheet metal field can transport noise into the interior space of the aircraft. If, for example, the noise reduction system is arranged in the sheet metal field, then the noise source or the energy input of said sheet metal field to the cabin interior can be reduced. Moreover, further application options of the noise reduction system are imaginable where noise sources emit interfering noises that are to be damped.

According to a further exemplary embodiment, the noise reduction system comprises a control unit. The control unit can control the counter sound source such that the noise intensity and the counter sound intensity can be reduced. By the control unit it is possible, for example, to transmit various pre-definitions from reference databases or other desired control signals to the counter sound source, as a result of which a desired sound reduction becomes possible. It is thus imaginable that due to the measured noise intensity and counter sound intensity by the intensity sensor, by comparison with a reference database it is possible to determine whether detrimental noises or defects are present in the means of transport. For example, noises that indicate a defect, for example a damaged ball bearing, can be detected on the basis of the measured sound intensity of the counter sound source and of the noise source. This provides a simple possibility of reducing noise and in addition of determining the availability of systems of a means of transport.

According to a further exemplary embodiment, the noise reduction system comprises a multitude of counter sound sources and a multitude of intensity sensors. The control device is then equipped such that, based on a measured multitude of noise intensities and counter sound intensities, each of the multitude of counter sound sources, corresponding to their positions, is controllable by the control unit. Thus, the sound energy input of the noise source can be globally reduced by the multitude of counter sound sources. If there are several noise sources in a vehicle, then by the present invention a counter sound source with an intensity sensor can be affixed in front of each noise source, so that in a targeted manner each noise source per se can be actively reduced. The control unit can receive data from all the counter sound sources and intensity sensors, and, based on the position of the counter sound sources in the interior space, can emit a control signal for each individual one of the multitude of counter sound sources, so that an optimal result of noise reduction can be implementable.

According to a further exemplary embodiment, the means of transport is selected from the group comprising motor vehicles, rail vehicles, aircrafts and water crafts. It is thus possible to equip any type of means of transport with the noise reduction method according to the invention, as a result of which the comfort of travelling within an interior space of a means of transport listed above is significantly improved due to active noise reduction.

The embodiments of the device also apply to the method, to the means of transport, and to its use, and vice versa.

BRIEF DESCRIPTION OF THE DRAWINGS

Below, for further explanation and to provide a better understanding of the present invention, exemplary embodiments are described in more detail with reference to the enclosed drawings. The following are shown.

DETAILED DESCRIPTION

Figure 1:
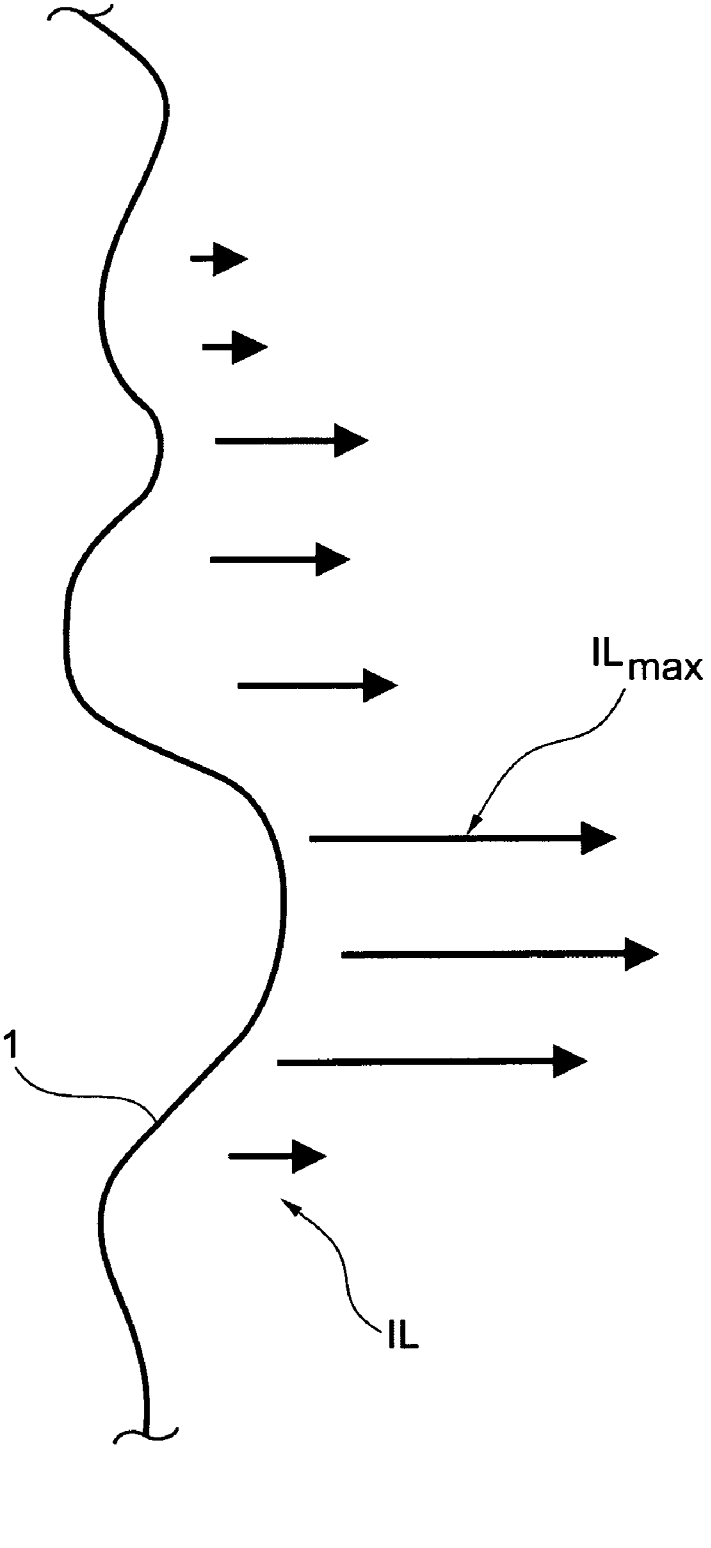
FIG. 1 a diagrammatic view of a noise source with a radiating noise intensity.

Identical or similar components in different figures have the same reference characters. The illustrations in the figures are diagrammatic and not to scale.

Figure 2:
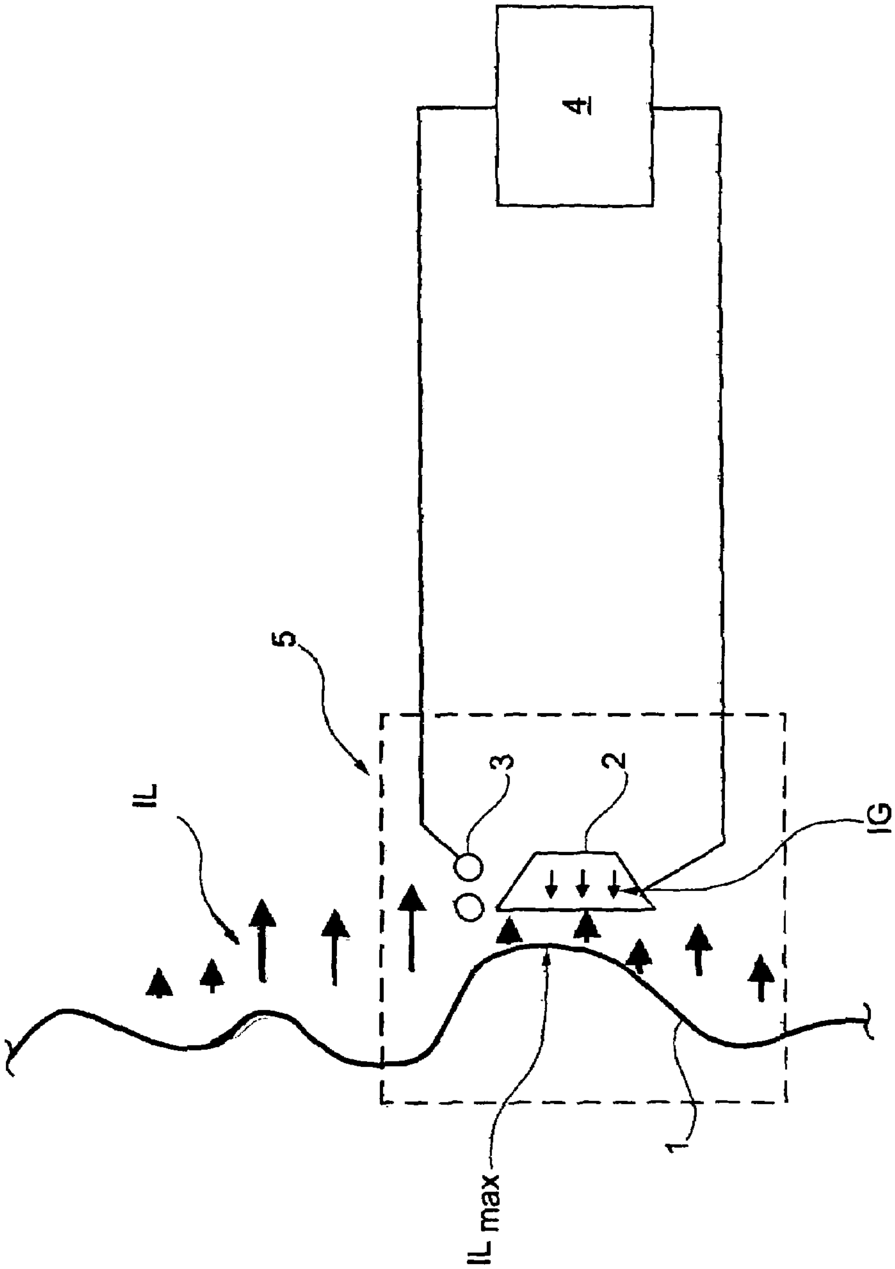
FIG. 2 a diagrammatic view of an exemplary embodiment of the present invention, in which a counter sound source is arranged in front of a noise source that radiates an intensity.

FIG. 2 shows an exemplary embodiment of the noise reduction system for actively blocking a noise source 1 for a means of transport. The noise reduction system comprises at least one counter sound source 2 and at least one intensity sensor 3. The at least one counter sound source 2 and the at least one intensity sensor 3 are installed in a measuring region 5. In the measuring region 5 measuring the noise intensity IL of the noise source 1 and measuring the counter sound intensity IG of the counter sound source 2 can be provided by the intensity sensor 3. On the basis of the measured noise intensity IL and of the counter sound intensity IG, the counter sound source 2 is controllable such that the sound energy input of the noise source 1 can be globally reduced by the counter sound source 2.

In this arrangement the measuring region 5 defines the region in which the at least one intensity sensor 3 can measure a noise intensity IL of the noise source 1 and a counter sound intensity IG of the counter sound source 2.

FIG. 1 describes a noise source 1, for example a sheet metal field, and the noise intensity IL that radiates from it. In the region of the largest vibration of the sheet metal field, for example the maximum noise intensity $IL_{max}$ is radiated into an interior space.

FIG. 2 shows the noise source 1, for example a sheet metal field, and its radiating noise intensity IL, as is also described in FIG. 1. Moreover, in FIG. 2 the noise reduction system according to the invention is arranged. In this setup the counter sound sensor 2 is arranged in the measuring region 5. According to the exemplary embodiment in FIG. 2, the counter sound source 2 is, for example, affixed to the noise source 1 where said noise source 1 radiates the maximum noise intensity $IL_{max}$. In this way good damping or muffling results are achieved, including global ones.

In this arrangement the counter sound source 2 is designed to radiate a counter sound intensity IG. Radiation of the noise intensity IG can preferably be in the direction of the noise source 1. In this way improved muffling results are achieved.

As shown in FIG. 2, the directions of the arrows denoting noise intensity indicate a directed direction of radiation of the noise intensity IL and of the counter sound intensity IG. In each instance both intensities IG, IL propagate away from the noise source 1 and the counter sound source 2 so that positive measuring of the sound intensities is provided. This results in improved muffling results, in contrast to a negative counter sound source 2, which has an absorbing effect (direction of arrows towards the centre).

As shown in FIG. 2, the sound intensity sensor 3 is arranged in the measuring region 5 so that measuring the noise intensities IL, IG becomes possible. The sound intensity sensor 3 can preferably be affixed on the side of, or behind, the counter sound source 2. Improved measuring of the sum of the noise intensity IL and the counter sound intensity IG is therefore possible.

Furthermore, as shown in FIG. 2, the sound intensity sensor 3 can be linked to the counter sound source 2 by way of a control unit 4. By the control unit 4 it is possible, for example, to compare the measured values of the intensity sensors 3 with predefined measuring values of a database so that an evaluation of abnormal intensity values is possible. Thus with this embodiment of the noise reduction system it is possible to analyse damages in a means of transport, which damage usually cause abnormal sounds.

Figure 3:
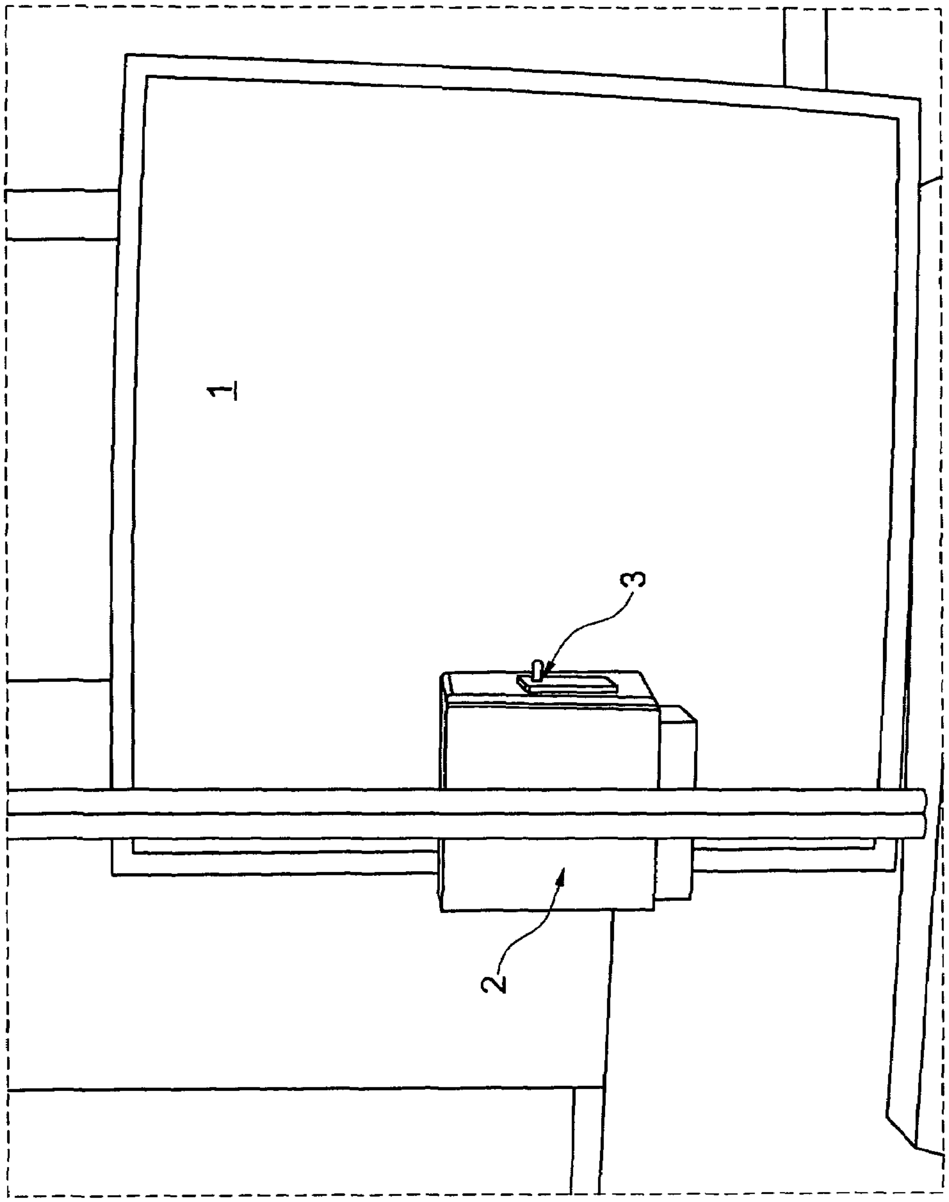
FIG. 3 a diagrammatic view of an experimental setup according to an exemplary embodiment of the present invention, in which embodiment a counter sound source with intensity sensors is placed in front of a noise source.

FIG. 3 shows an exemplary experimental setup according to the present invention. A sheet metal field is provided as a noise source 1. The counter sound source 2 with an intensity sensor 3 is placed close to the surface of said noise source 1, for example in a region of 0 to 5 cm (centimeters), 5 to 15 cm (centimeters) or 0 up to 1 meter. The intensity sensor 3 measures the noise intensity IL and the counter sound intensity IG and from this in turn controls the counter sound source 2 such that the sound energy input of the noise source 1 or of the sheet metal field can be reduced. As shown in FIG. 3, the intensity sensor 3 can be arranged directly on the counter sound source 2, for example as a single piece or as a unit. Thus a compact noise reduction device is created that can be installed at any desired locations in front of a noise source 1.

Figure 4:
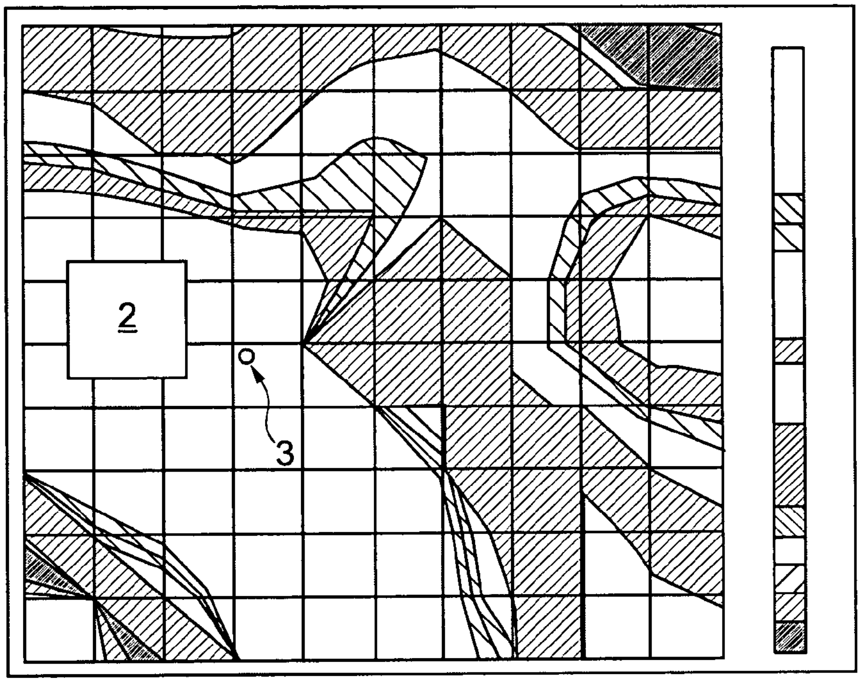
FIG. 4 a diagrammatic view of a measuring result of the sound energy input of a noise source without active noise reduction according to the present invention.
Figure 5:
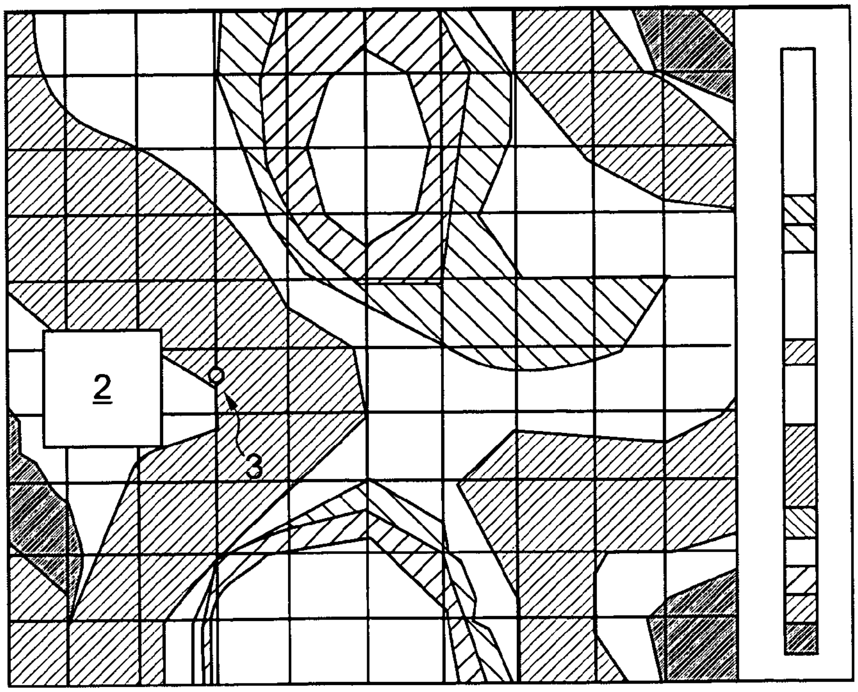
FIG. 5 a diagrammatic view of a measuring result of an experimental setup according to FIG. 4, in which experimental setup the sound energy input is reduced by activation of the noise reduction system according to an exemplary embodiment.

FIGS. 4 and 5 show an evaluation of measuring results, wherein the noise reduction system is inactive in FIG. 4 and active in FIG. 5. In these diagrams the bright areas show a region with a high intensity level, while the dark areas indicate a low sound intensity level. The noise source generates a directed noise intensity from the left-hand margin to the right-hand margin.

As shown in FIG. 4, the counter sound source 2 and the intensity sensor 3 are affixed in close proximity, or in the left-hand region, in front of the noise source 1. In an uncontrolled sound field, or with sound reduction systems inactive, it becomes clear that in the left-hand region bright areas are generated that indicate a high sound intensity.

FIG. 5 illustrates a sound field which, controlled by the sound reduction system according to the invention, is actively reduced. The diagram shows that dark regions arise in the region of the intensity sensor 3, which dark regions indicate low sound intensities. This makes it possible for the sound intensity sensor 3 to permanently take measurements of the noise intensity IL of the noise source 1, and of the counter sound intensity IG of the counter sound source 2, and based on these measurements to control the counter sound source 2. Although this provides only a local effect due to the counter sound source 2, it can result in global noise reduction as illustrated by the dark region in FIG. 5.

In the experimental setup according to FIG. 3, in which the counter sound source 2 with the intensity sensor 3 has been positioned in front of the noise source 1 such that the region of the largest energy input is covered, for example a global noise reduction of up to 12 dB is possible in an interior space. Furthermore, for example, noise reduction values of 20 dB, 40 dB or 60 dB [decibels] are also achievable.

In addition, it should be pointed out that "comprising" does not exclude other elements or steps, and "a" or "one" does not exclude a plural number. Furthermore, it should be pointed out that characteristics or steps which have been described with reference to one of the above exemplary embodiments can also be used in combination with other characteristics or steps of other exemplary embodiments described above. Reference characters in the claims are not to be interpreted as limitations.

LIST OF REFERENCE CHARACTERS

1 Noise source
2 Counter sound source
3 Intensity sensor
4 Control unit
5 Measuring region
IL Intensity of the noise source
$IL_{max}$ Maximum intensity of the noise source
IG Intensity of the counter sound source

The invention claimed is:

1. A noise reduction system for actively blocking a noise source for a means of transport, wherein the noise reduction system comprises:
- at least one counter sound source; and
- at least one intensity sensor;
- wherein the at least one counter sound source and the at least one intensity sensor are arranged in a measuring region;
- wherein in the measuring region, the intensity sensor is adapted to measure the noise intensity of the noise source and the counter sound intensity of the counter sound source;
- wherein based on the measured noise intensity and the counter sound intensity, the counter sound source is controllable such that the sound energy input of the noise source can be globally reduced by the counter sound source by reducing the sound energy input in front of the noise source;
- wherein the at least one intensity sensor is installed, in the direction of the sound propagation from the noise source, behind the at least one counter sound source;
- wherein the counter sound source is adapted to provide the direction of sound propagation of the counter sound source in the direction of the noise source towards the noise source; and
- wherein the intensity of the noise source and the intensity of the counter sound source are directed opposite to each other.

2. The noise reduction system of claim 1,
- wherein the at least one intensity sensor is adapted to measure the noise intensity and the counter sound intensity with a positive operational sign.

3. The noise reduction system of claim 1,
- wherein the at least one intensity sensor is adapted to form an integral unit with the at least one counter sound source.

4. The noise reduction system of claim 1,
- wherein the counter sound source is adapted to cover the region of the greatest energy input of the noise source.

5. The noise reduction system of claim 1,
- wherein the intensity sensor comprises one or more of two-microphone technique sensors for measuring sound pressure and sound velocity.

6. The noise reduction system of claim 1,
- wherein the noise source comprises one or more area radiators, sheet metal fields, aircraft fuselages, motor vehicle bodies and drive noises.

7. The noise reduction system of claim 1, further comprising:
- a control unit;
- wherein by the control unit the counter sound source is controllable such that the noise intensity and the counter sound intensity can be reduced.

8. The noise reduction system of claim 7, further comprising:
- a plurality of counter sound sources;
- a plurality of intensity sensors;
- wherein the control unit is equipped such that, based on a measured plurality of noise intensities and counter sound intensities, each of the counter sound sources, corresponding to their positions, is controllable by the control unit so that the sound energy input of the noise source can be globally reduced by the counter sound sources.

9. A noise reduction method for actively blocking a noise source for a means of transport, comprising:

arranging at least one counter sound source and at least one intensity sensor in a measuring region;

wherein the at least one intensity sensor is installed, in the direction of the sound propagation from the noise source, behind the at least one counter sound source;

wherein the counter sound source is adapted to provide the direction of sound propagation of the counter sound source in the direction of the noise source towards the noise source; and wherein the intensity of the noise source and the intensity of the counter sound source are directed opposite to each other;

measuring the noise intensity of the noise source and the counter sound intensity of the counter sound source by the intensity sensor in the measuring region; and controlling the counter sound source based on the measured noise intensity and on the counter sound intensity, such that the sound energy input of the noise source is globally reduced by the counter sound source by reducing the sound energy input in front of the noise source.

10. An aircraft comprising a noise reduction system, the noise reduction system comprising:

at least one counter sound source;

at least one intensity sensor;

wherein the at least one counter sound source and the at least one intensity sensor are arranged in a measuring region;

wherein in the measuring region, the intensity sensor is adapted to measure the noise intensity of the noise source and the counter sound intensity of the counter sound source;

wherein based on the measured noise intensity and the counter sound intensity, the counter sound source is controllable such that the sound energy input of the noise source can be globally reduced by the counter sound source by reducing the sound energy input in front of the noise source;

wherein the at least one intensity sensor is installed, in the direction of the sound propagation from the noise source, behind the at least one counter sound source;

wherein the counter sound source is adapted to provide the direction of sound propagation of the counter sound source in the direction of the noise source towards the noise source; and wherein the intensity of the noise source and the intensity of the counter sound source are directed opposite to each other.

* * * * *